United States Patent [19]
Herlihy et al.

[11] Patent Number: 5,361,765
[45] Date of Patent: Nov. 8, 1994

[54] TWO-PART QUADRATURE NMR COIL

[75] Inventors: David J. Herlihy, New Berlin; Eddy B. Boskamp, Menomonee Falls, both of Wis.

[73] Assignee: Medical Advances, Inc., Milwaukee, Wis.

[21] Appl. No.: 57,939

[22] Filed: May 7, 1993

[51] Int. Cl.$^5$ .............................................. A61B 5/055
[52] U.S. Cl. .................... 128/653.5; 324/318; 324/322
[58] Field of Search .................... 128/653.2, 653.5; 324/318, 322

[56] References Cited
U.S. PATENT DOCUMENTS

| | | | |
|---|---|---|---|
| 4,712,067 | 12/1987 | Roschmann et al. | 324/318 |
| 4,740,751 | 4/1988 | Misic et al. | 324/318 |
| 4,879,516 | 11/1989 | Mehdizadeh et al. | 324/318 |
| 5,221,902 | 6/1993 | Jones et al. | 324/318 |
| 5,256,971 | 10/1993 | Boskamp | 324/318 |
| 5,261,403 | 11/1993 | Saito et al. | 128/653.5 |
| 5,274,332 | 12/1993 | Jaskocski et al. | 324/318 |

*Primary Examiner*—Ruth S. Smith
*Attorney, Agent, or Firm*—Quarles & Brady

[57] ABSTRACT

A quadrature local coil includes a bifurcated first loop positioned on one side of the patient and sensitive to RF magnetic flux generally parallel to the surface of the loop and a second loop positioned on the other side of the patient, opposed to the first loop and sensitive to RF magnetic flux within the patient perpendicular to that to which the first loop is sensitive. In one embodiment, the first and second loops are mounted in opposing concave shells held against and supported by the patient.

7 Claims, 4 Drawing Sheets

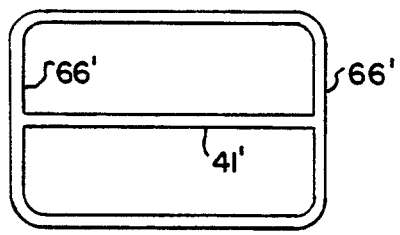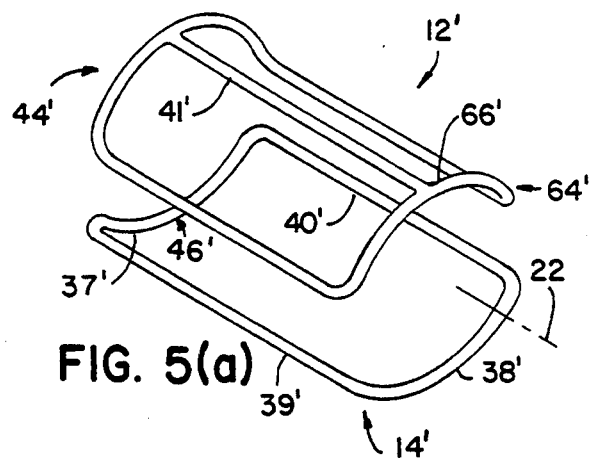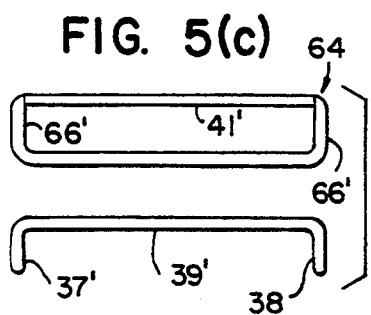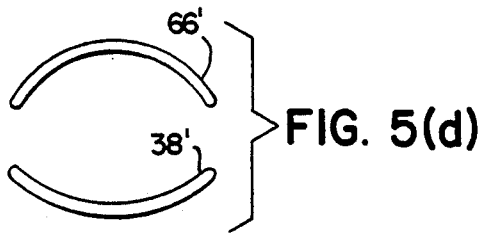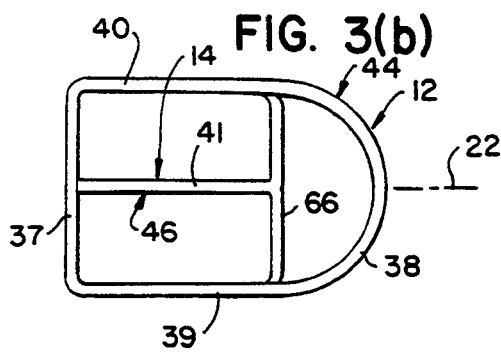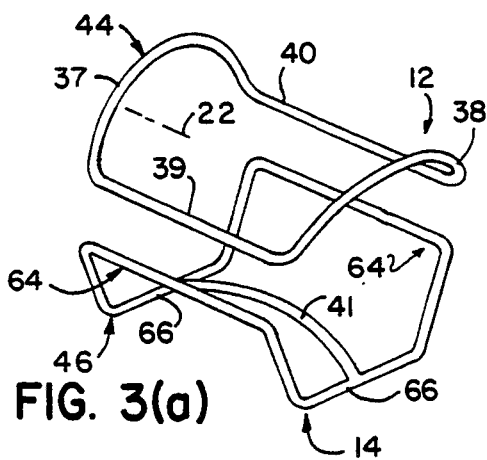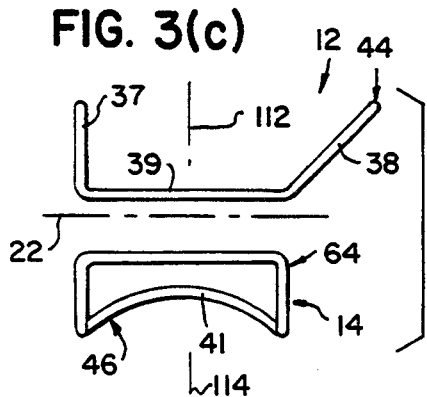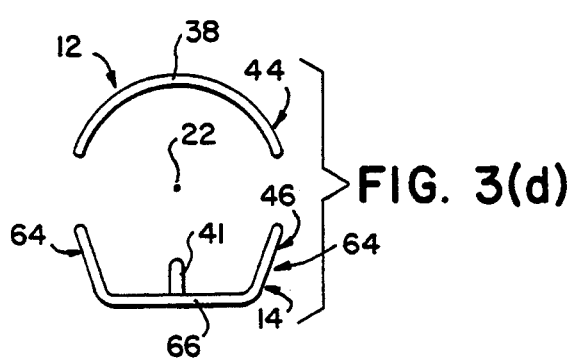

TWO-PART QUADRATURE NMR COIL

BACKGROUND OF THE INVENTION

1. Field of the Invention

The field of the invention is magnetic resonance imaging (MRI) and, in particular, local coils for use in receiving MRI signals.

2. Background Art

A. MRI Imaging

In MRI, a uniform magnetic field $B_0$ is applied to an imaged object along the z axis of a Cartesian coordinate system, the origin of which is approximately centered within the imaged object. The effect of the magnetic field $B_0$ is to align the object's nuclear spins along the z axis.

In response to a radio frequency (RF) excitation signal of the proper frequency, oriented within the x-y plane, the nuclei precess about the z-axis at their Larmor frequencies according to the following equation:

$$\omega = \gamma B_0 \quad (1)$$

where $\omega$ is the Larmor frequency, and $\gamma$ is the gyromagnetic ratio which is a constant and a property or the particular nuclei.

Hydrogen, and in particular the nucleus (protons), because of its relative abundance in biological tissue and the properties of its nuclei, is of principle concern in such imaging. The value of the gyromagnetic ratio $\gamma$ for protons is 4.26 kHz/gauss and therefore, in a 1.5 Tesla polarizing magnetic field $B_0$, the resonant or Larmor frequency of protons is approximately 63.9 MHz.

In a typical imaging sequence for an axial slice, the RF excitation signal is centered at the Larmor frequency $\omega$ and applied to the imaged object at the same time as a magnetic field gradient $G_z$ is applied. The gradient field $G_z$ causes only the nuclei, in a slice with a limited width through the object along an x-y plane, to have the resonant frequency $\omega$ and to be excited into resonance.

After the excitation of the nuclei in this slice, magnetic field gradients are applied along the x and y axes. The gradient along the x axis, $G_x$, causes the nuclei to precess at different frequencies depending on their position along the x axis, that is, $G_x$ spatially encodes the precessing nuclei by frequency. The y axis gradient, $G_y$, is incremented through a series of values and encodes the y position into the rate of change of phase of the precessing nuclei as a function of gradient amplitude, a process typically referred to as phase encoding.

A weak nuclear magnetic resonance generated by the precessing nuclei may be sensed by the RF coil and recorded as an NMR signal. From this NMR signal, a slice image may be derived according to well known reconstruction techniques. An overview of NMR image reconstruction is contained in the book "Magnetic Resonance Imaging, Principles and Applications" by D. N. Kean and M. A. Smith.

B. Local Coils

The quality of the image produced by MRI techniques is dependent, in part, on the strength of the NMR signal received from the precessing nuclei. For this reason, it is optimal to use an independent RF receiving coil placed in close proximity to the region of interest of the imaged object in order to improve the strength of this received signal. Such coils are termed "local coils" or "surface coils". The smaller area of the local coil permits it to accurately focus on NMR signals from the region of interest. Further, the RF energy of the field of such a local coil is concentrated in a smaller volume giving rise to improved signal-to-noise ratio in the acquired NMR signal.

The signal-to-noise ratio of the NMR signal may be further increased by orienting two coils pairs at 90° angles about the imaged object so that each detects RF energy along one of a pair of mutually perpendicular axes. This technique is generally known as quadrature detection and the signals collected are termed quadrature signals.

The outputs of the quadrature coil pairs are combined so as to increase the strength of the received signal according to the simple sum of the output signals from the coils. The strength of the uncorrelated noise component of these signals, however, will increase only according to the square root of the sum of the squares of the noise components. As a result, the net signal-to-noise ratio of the combined quadrature signals increases by approximately $\sqrt{2}$ over the signal-to-noise ratio of the individual signal.

The quadrature orientation of the two coils introduces a 90° phase difference between the NMR signals detected by these coils. Therefore, combining the outputs from the two quadrature coils, to achieve the above described signal-to-noise ratio improvement, requires that one signal be shifted to have the same phase as the other signal so that the amplitudes of the signals simply add.

Such phase shifting and combining is typically accomplished by means of a hybrid network. Hybrid networks are four-port networks known in the art and having the property that when the four ports are properly terminated, energy input to two of the ports, with the proper relative phase angles, will be combined at one of the remaining two ports. The antenna coils are attached to two of the ports and the output lead is attached to a third port and produces the sum of the signals from the antenna coils, one being shifted so that they add in-phase. The remaining uncommitted port is connected to a termination resistor.

As used herein, the term quadrature coil and quadrature signal, will refer to the detecting of the NMR signal along multiple axes and combining the signals so collected, with the appropriate phase shifts to produce a signal of improved signal-to-noise ratio.

C. Planar Coils

The use of volumetric quadrature coils of conventional design may be undesirably constraining to the patient who must be surrounded by four orthogonal coils within the relatively small volume of the magnet bore. Further, in order that the local coil may be conveniently located on the patient, it is necessary that the quadrature local coil be separable or slidable to enclose the desired anatomy.

It is known, therefore, for certain imaging applications such as the imaging of the spine, to construct a quadrature local coil on a substantially planar cradle to be attached to the upper surface of the patient support table so that the patient may simply lie on top of the coil and so that the coils structure is not unduly constraining. Such open coils are termed "planar" coils to distinguish them from "whole volume" coils such as might be constructed of opposed saddle coils or solenoids. The prior art has recognized the desirability of a quadrature, planar coil. See, for example, U.S. Pat. No. 5,030,915, issued July 9, 1991 to Boskamp, hereby incorporated by reference.

In such quadrature planar coils, a coil pair is disposed so as to have a sensitivity to flux within a region of interest directed along planes parallel to the plane of that pair. A third coil also positioned within the plane and typically between the coils of the pair has a sensitivity normal to the plane of the pair to produce a signal in quadrature from the pair. Thus, a quadrature coil can be realized from coils disposed substantially within a single plane on one side of the patient.

Critical to the operation of a quadrature planar coil is isolation between the coil pair and the third coil. This isolation is obtained by accurately aligning the third coil between the coil pair and affixing both to a single rigid surface. A drawback to the quadrature planar coil is that its region of sensitivity is concentrated closely to the plane where all the coils are attached.

SUMMARY OF THE INVENTION

The present invention recognizes that the third coil of a quadrature planar coil may be placed on the opposite side of the body from the coil pair to advantageously move the coil's region of sensitivity away from the plane of the pair. This movement improves the isolation between the third coil and the coil pair in the presence of some misalignment between these parts, allowing greater flexibility in the design of coils support structure.

Specifically, the present invention includes a first loop positioned adjacent to an imaging volume and having a first reception pattern which couples to a magnetic field of a having a first orientation. A second loop, opposed substantially symmetrically to the first loop about the imaging volume, has a diametric conductor to divide it into a pair of coils. The pair of coils has a second reception pattern which couples to a magnetic field of a second orientation within the imaging volume and having an angular separation from the first orientation. Typically, the angular separation is 90°.

It is thus one object of the invention to produce a quadrature coil having its components separated into two planes and thus providing improved access to the patient.

The first loop may be held by a first arched support with a first concave surface sized to fit against an anterior surface of the patient. The second loop may be held by a second arched support also having a concave surface, but sized to fit against a posterior surface of the patient, and opposing the first arched support. A clamping system may be used to draw the first and second arched supports together about the patient wherein the first and second concave surfaces serve to support and align the first and second loops against the patient with the loops in alignment.

It is another object of the invention to provide a simple and flexible method of holding the coil adjacent to the patient. The reduced sensitivity of two part quadrature coil to misalignment between its halves allow the coils to be supported by the patient's body. Motion between the patient and the coils is thus reduced and positioning of the patient within the coil is greatly simplified.

It is yet another object of the invention to provide a quadrature coil that may be positioned to closely match the patient's anatomical shape regardless of the patient's size thus optimizing the signal-to-noise ratio. The ability to use the patient to support the coil parts provides ready and precise sizing of the coil to the patient and avoids the need for complicated and bulky positioning linkages between the two coil parts.

Other objects and advantages besides those discussed above will be apparent to those skilled in the art from the description of the preferred embodiment of the invention which follows. Thus, in the description, reference is made to the accompanying drawings, which form a part hereof, and which illustrate one example of the invention. Such example, however, is not exhaustive of the various alternative forms of the invention. Therefore, reference should be made to the claims which follow the description for determining the full scope of the invention.

BRIEF DESCRIPTION OF THE DRAWINGS

FIGS. 3(a) through 3(d) are perspective, plan, side elevation, and front elevation views respectively of posterior and anterior coils of the local coil of FIG. 1;

FIGS. 5(a) through 5(d) are perspective, plan, side elevation, and front elevational views of the posterior and anterior coils of FIG. 4;

DETAILED DESCRIPTION OF THE PREFERRED EMBODIMENT

Figure 1:
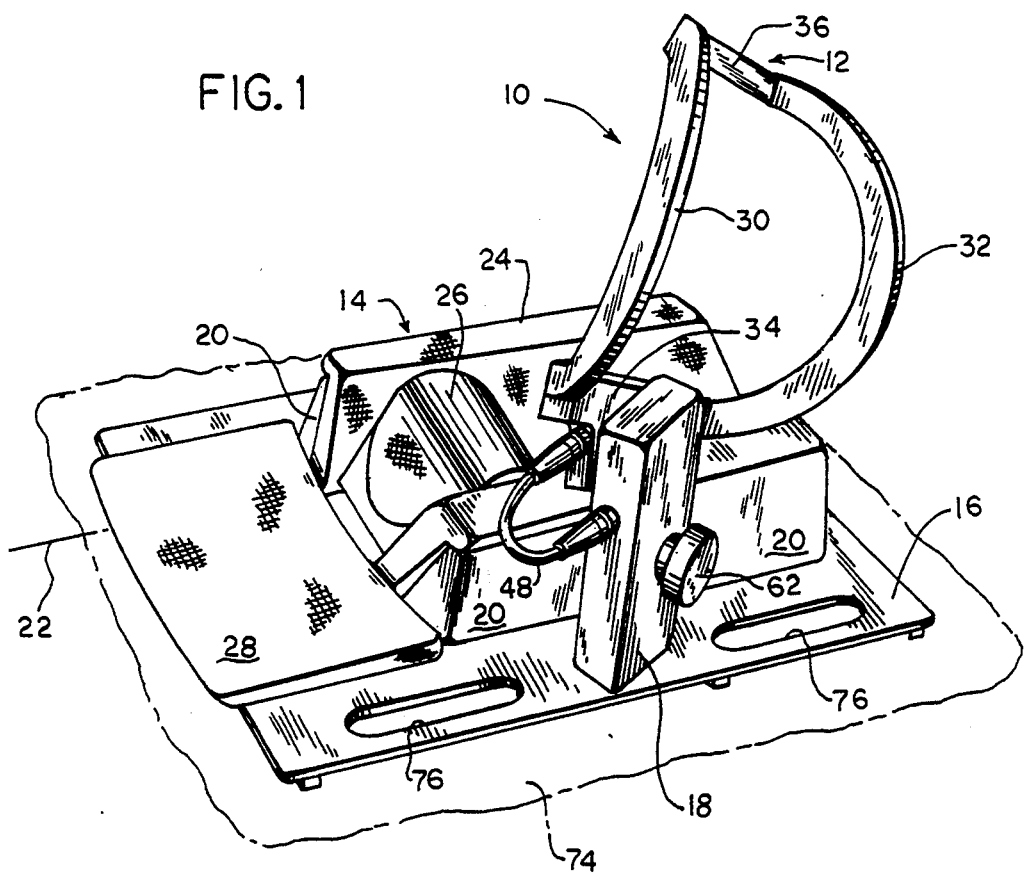
FIG. 1 is a perspective view of a housing supporting the local coil of the present invention as adapted for imaging of the neck and showing the posterior and anterior coils in the open position.
Figure 2:
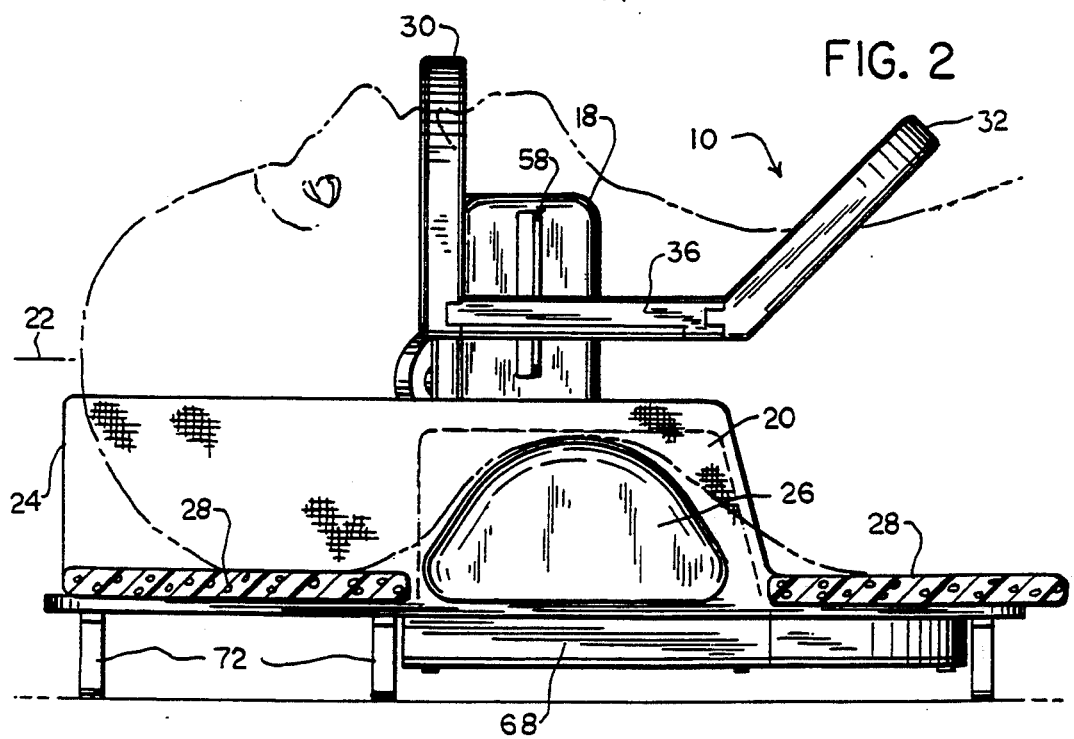
FIG. 2 is an elevation in cross-section along a midsagittal plane showing positioning of the local coil of FIG. 1 on a patient.

Referring to FIGS. 1 and 2, quadrature coil 10 of the present invention, when configured for use in neck imaging, includes opposed anterior and posterior coils 12 and 14. The posterior coil 14 is supported by a generally horizontal, planar base 16 whereas the anterior coil 12 is held away from the base 16 by an extension tower 18 projecting perpendicularly upward from the horizontal surface of the base 16. The base 16 has on its lower surface a number of downwardly extending arc shaped ribs 72 that fit against the concave upper surface of the MRI table 74 (shown in FIG. 1) to stiffen the base 16 and to provide additional support for the base 16 against the table 74. Also shown in FIG. 1, the base 16 includes cut out hand grips 76 which permit it to be readily removed from the table 74.

Referring to FIG. 2, when the local coil 10 is in use, the patient's head rests back against the upper surface of the base 16 with the patient's frontal plane generally parallel to the surface of the base 16. Left and right medially extending wedges 20 rise from the upper surface of the base 16. The wedges are symmetrically opposed about the medial axis 22 and support and position a trough shaped cushion 24 that cradles either side of the patient's neck and head when the patient is positioned in the coil 10. Held within the trough is a transverse hemicylindrical foam pad 26 which supports the back of the patient's neck and tips the patient's head to face substantially upward on the base 16. Flat foam cushions 28 are positioned against the base 16 above and below the hemicylindrical foam pad 26 along the medial axis 22, to support the back of the patient's head and shoulders.

The anterior coil 12 includes an arcuate nose arch 30 and chest arch 32 joined to each other at the arch ends by substantially straight left and right sidebar 34 and 36 which form a saddle shaped guide. The left sidebar 34 is attached to and may hinge about the extension tower 18 so as to move the anterior coil 12 into an open or closed position. In the closed position, the left and right sidebars 34 and 36 are parallel to the upper surface of the base 16 and positioned above the left and right wedges 20. In the closed position, the nose arch 30 extends downward around the patient's face in a transverse plane, and chest arch 32 extends downward around the patient's lower neck in a plane angled between the transverse and frontal planes.

As mentioned, the left side bar 34 of the anterior coil 12 is attached to a hinge (not shown) which permits the chest arch 32 to be retracted away from the point of patient entry when the anterior coil 12 is moved to the open position, thus improving the access for the patient who normally lays back against the base 16 and whose head enters the coil at a relatively steep angle. The above structural components are fabricated from a nonmagnetic, nonconductive, polymeric material to reduce their interaction with the magnetic and electrical fields of the MRI equipment. The mechanism of opening and adjusting the anterior coil 12 is described in detail in U.S. Pat. No. 5,166,618 entitled: "NMR Neck Coil with Passive Decoupling" hereby incorporated by reference.

Referring to FIGS. 1, 2 and 3(a) through 3(d), the anterior and posterior antenna coils 12 and 14 respectively include an anterior and posterior loop 44 and 46 formed of copper tubing. The anterior loop 44 conforms generally to the support structure of the anterior coil 12 and includes a conductor 37 formed in an arch to follow the arcuate nose arch 30 and a conductor 38 following the chest arch 32. These conductors 37 and 38 are joined into a loop by straight conductors 39 and 40 following the left and right sidebars 34 and 36 so that the conductors together form the generally saddle shaped loop 44.

Referring still to FIGS. 3(a)–(d), the posterior loop 46 include a left and right arcuate conductor 64 which rise on either side of the patient's neck when the patient is in position on the coil 10. These conductors 64 fit into channels in the left and right wedges 20. The left and right conductors 64 are connected by superior and inferior conductor segments 66 substantially parallel to the plane of the base 16 and contained beneath the base 16 in a protective housing 68.

Centered between left and right conductors 64 to connect the center of superior and inferior conductor segments 66 is neck arch conductor 41 which extends upward into the hemicylindrical foam pad 26 to a position adjacent to the posterior of the neck.

Figure 7:
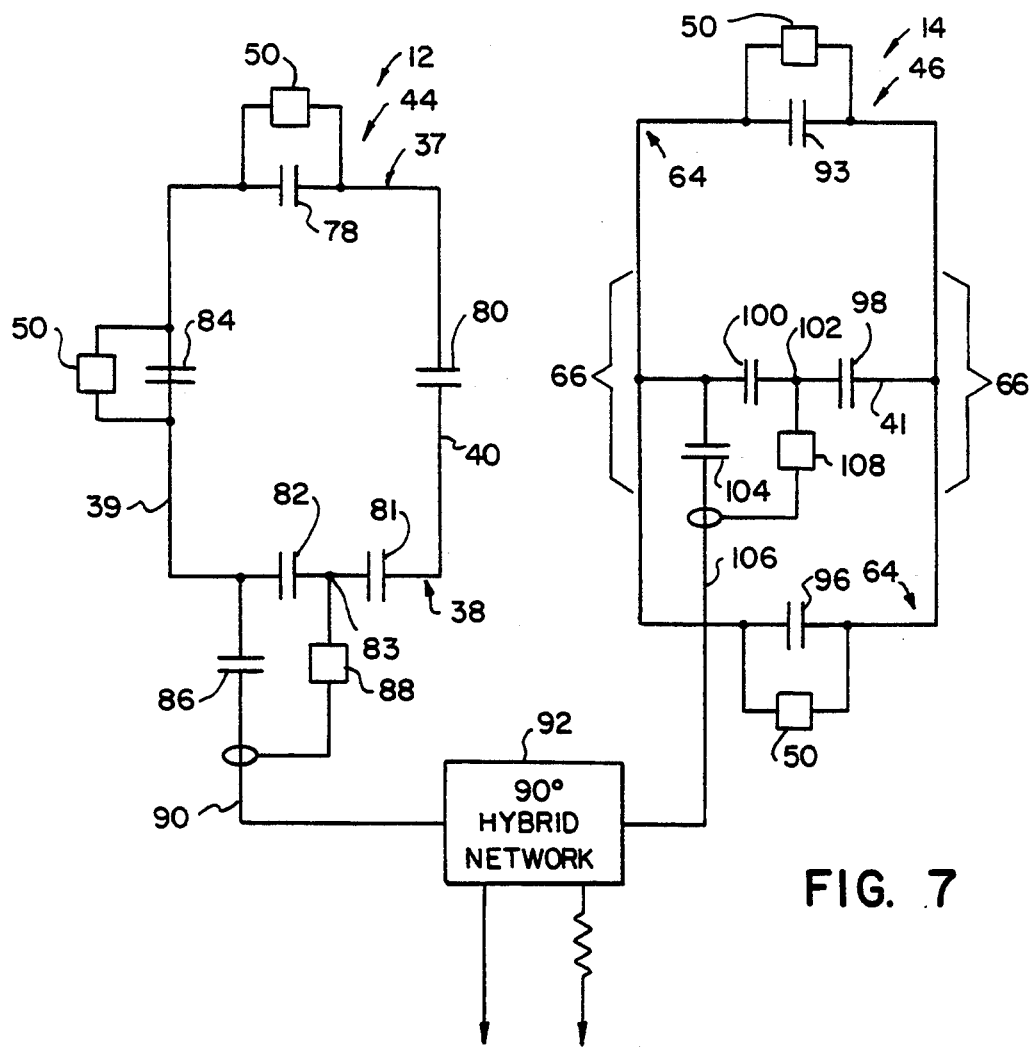
FIG. 7 is a simplified schematic of the conductors of the posterior and anterior coils of the present invention as joined by a combiner.

Referring to FIG. 7, the anterior loop 44 is cut at four points spaced approximately equal distances along the loop. These cuts are bridged by capacitors 78 through 84. These cut points will be termed interfaces, and the capacitors 78 through 84 bridging the cut points will be termed interface capacitors. Each interface is bridged by one interface capacitor except for the interface in the conductor 38 which is bridged by a series connection of capacitors 82 and 81 whose junction provides a loop ground 83. Interface capacitor 78 is placed approximately midpoint along conductor 37, interface capacitor 84 is placed approximately midpoint along conductor 39, interface capacitor 80 is placed approximately midpoint along conductor 40, and junction 83 is placed approximately midpoint along conductor 38.

The sections of the anterior loop 44 between interface capacitors 78 through 84 provide inductance which together with the capacitance of the interface capacitors 78 through 84 tune the anterior loop 44 into resonance at the Larmor frequency of the MRI equipment. An NMR signal may be developed from the anterior loop 44 across capacitor 82. The signal is received by a co-axial cable 90 through coupling capacitor 86 which is connected to one side of capacitor 82. The other side of capacitor 82, being the loop ground 83, is connected to the shield of coaxial cable 90 after passing through RF tank circuit 88. The signal from anterior loop 44 is conducted via coaxial cable 90 to one port of a four port 90° hybrid network 92 which will be described further below.

Shunting interface capacitor 78 and 84, and thus connected in parallel with interface capacitor 78 and 84 are passive decoupling networks 50. Decoupling networks 50 comprise back-to-back diodes in series with inductances (not shown) which together insert the inductance in parallel with its respective interface capacitors 78 or 84 when the voltage across that interface capacitance is sufficient to bias the diodes into conductance. The inductor is sized so as to create a parallel resonance circuit with its associated capacitance 78 or 84 and thus to block current flow in the anterior loop 44, effectively decoupling the anterior loop 44 from large amplitude radio frequency signals at the Larmor frequency as are typically are present during the excitation stage of an MRI pulse sequence. The magnitude of the much lower strength RF signals seen during the detection of the NMR signal from the precessing nuclei is such as to provide insufficient voltage to bias the diodes into conductance thereby not placing the inductor into parallel resonance during the detection phase. A detailed description of such isolation networks and the selection of the components for them is contained in the above referenced U.S. Pat. No. 5,166,618.

The posterior antenna loop 46 is broken at three points, the first two spaced approximately at the midpoints of conductors 64 and the third point being spaced midway along of neck arch conductor 41. Interface capacitors 93 and 96 join the cuts in the conductors 64 and interface capacitors 98 and 100, as connected in series to join at a loop ground 102, are connected across the cut in the neck arch conductor 41. Interface capacitors 93 through 100 are sized so as to produce a resonance with the inductance of the conductors at the Larmor frequency of the precessing nuclei in a mode having countercyclic currents flowing through two loops formed by the bisection of the posterior loop 46 by the neck arch conductor 41, i.e., the first loop comprising one loop 64 together with half of the inferior and superior segments 66 joining it to the neck arch conductor 41 and the neck arch conductor 41, and the second loop comprising the other loop 64 together with the remaining halves of the inferior and superior segments 56 joining it to neck arch conductor 41 and the neck arch conductor 41. The neck arch conductor 41 is shared by the two loops and in this resonant mode receives confluent currents from the two loops. That is, the countercyclic currents in the first and second loops at this resonant mode join and add through neck arch conductor 41, flowing in the same direction.

A signal from loop 46 is developed across interface capacitor 100. A co-axial cable 106 is joined through coupling capacitor 104 to one side of interface capacitor 100 and at its shield to the other side of interface capacitor 100, being the loop ground 102, through RF tank circuit 108. The signal so developed is proportional to the currents flowing through the neck arch conductor 41.

As before, decoupling networks are placed across selected capacitors 93 and 96 so as to decouple the posterior loop 46 from potentially damaging currents during the RF excitation portion of the MRI sequence. Coaxial cable 106 connects to 90° hybrid network 92 at a second port so as to combine its signal with the signal on coaxial cable 90, so that one such signal is shifted by 90°. The sum of these signals, one shifted, are presented out of a third port of the hybrid network 92. The hybrid network 92 thus combines the signals on coaxial cables 90 and 106 in quadrature as is well understood in the art.

Figure 8:
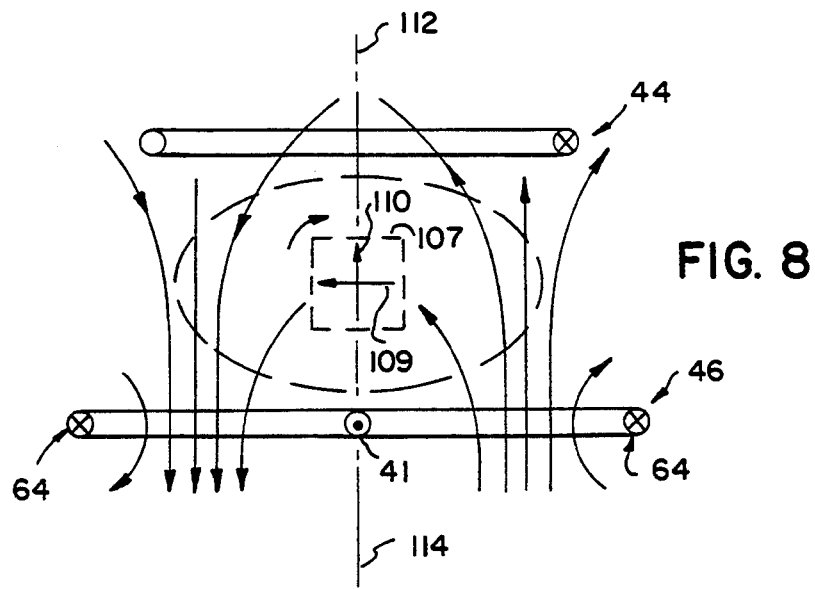
FIG. 8 is a simplified transverse cross sectional view of the conductors of the present invention when in position about a patient.

Referring now to FIG. 8, nuclear spins within a region of sensitivity 107 in the patient, producing a clockwise rotating magnetic vector, will induce co-cyclic currents in the two loops formed by the bisection of the neck arch conductor 41 in the posterior loop 46. These currents will vary in magnitude depending on the deviation of the rotating vector from a horizontal plane 109 generally parallel to the patient's frontal plane. The rotating vector will also induce a current in anterior loop 44, the magnitude of which will be dependent on the deviation of the rotating magnetic vector from a vertical orientation 110.

The region of interest is centered about an axis 114 of the posterior loop 46 and an axis 112 of the anterior loop, the axes approximating axes of radial symmetry of the loops 44 and 46. When the axis 112 of the anterior loop 44 and axis 114 of the posterior loop 46 are coaxial, the loops 44 and 46 are isolated from each other because the flux generated by current flow in the anterior loop 44 falls equally within the two loops of posterior loop 46, thus generating no net current flow when the current of the two loops sums in the neck arch conductor 41. And conversely, the flux generated by current flow in the posterior loop 46 passes symmetrically in both directions through anterior loop 44 thus generating no current in anterior loop 44. This condition obtains only when the axes 112 and 114 of the anterior and posterior loops 44 and 46 are perfectly aligned. However, it has been determined that the attenuation of the flux fields from the coils, caused by the interposition of the patient between the loops 44 and 46, loosens this requirement of co-axial alignment sufficiently that the loops 44 and 46 remain substantially isolated with less than perfect alignment of their axes 112 and 114. This aspect is critical for use of the coils in imaging of the pelvic region or any region which suggests the use of flexible coils as now shown in FIG. 4.

Figure 4:
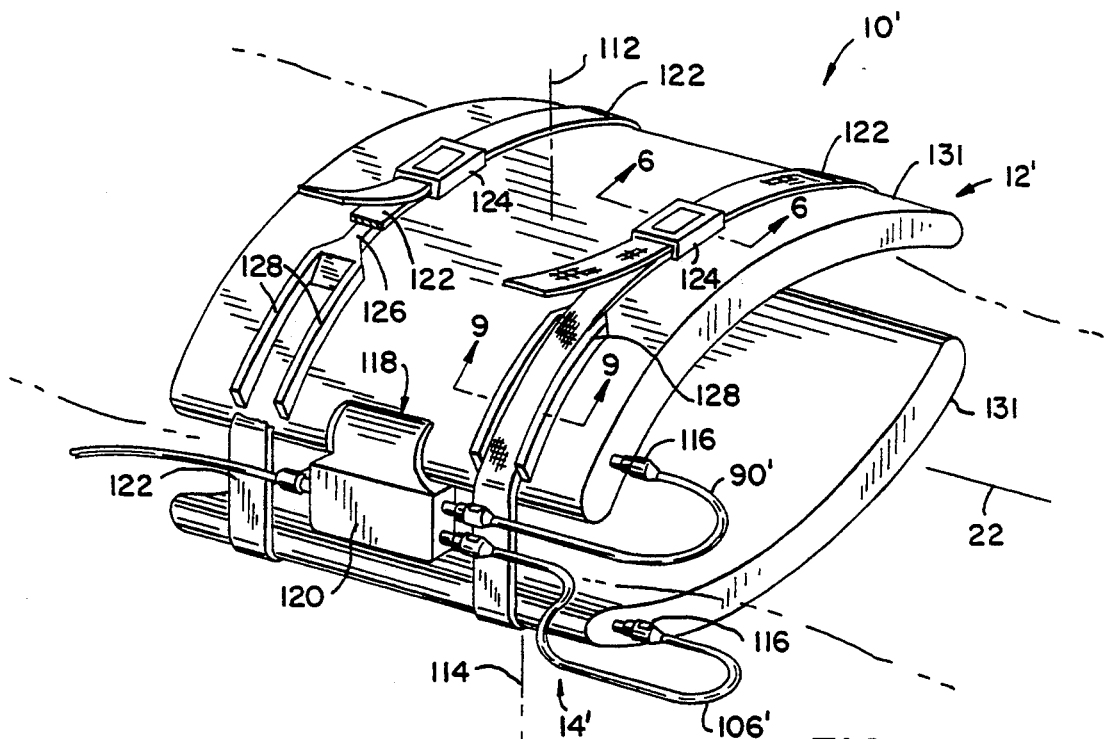
FIG. 4 is a perspective view of a second embodiment of the local coil of the present invention for use in pelvic imaging showing the posterior and anterior coils in the closed position as held against the patient by retaining straps.

Referring to FIG. 4, for imaging the pelvis the anterior and posterior coils 12' and 14' are defined by hemicylindrical shells 131 having concave inner surfaces abutting the anterior and posterior of the pelvis respectively. The shells 131 are constructed of a nonconductive plastic material to provide support for internal conductors.

Electrical connectors 116 attach to a superior edge of each shell 131 of coils 12' and 14' to provide access to the signals developed by each coil 12' and 14'. Cables 90' and 106' attached to the electrical connectors 116 receiving signals from the anterior and posterior coils 12' and 14' respectively connect to the hybrid network 92 for combining as has been described.

A hinge 118 attached to a distal edge of the hemicylindrical shell 131 of the anterior coil 12' supports a housing 120 which contains the hybrid network 92 such has been described above. The hinging of the housing 120 against the anterior coil simplifies the connection of the leads to the housing 120 and the positioning of the shells about the patient but allows the housing 120 to be folded against the patient to reduce the cross section of the coil for insertion into the bore of the MRI system and to better match differing anatomical shapes.

Straps 122 wrap circumferentially around the shells 131 of the anterior and posterior coils 12' and 14' to hold them snugly against the patient after they have been positioned so that their axes 112 and 114 of the contained coils are appropriately aligned. The straps 122 are tightened by means of conventional buckles 124 which expose one end of each strap 122 that may be grasped for cinching the straps 122 tightly around the shells 131.

In the preferred embodiment, two straps 122 are employed separated along the superior inferior axis of the patient to provide a distributed force against the shells 131 and an even force against the patient. The hemicylindrical shape of the shells 131 allow them to be supported simply against the patient without the use of other alignment or support means to ensure rough alignment of the axes 112 and 114 of the coils.

Figure 6:
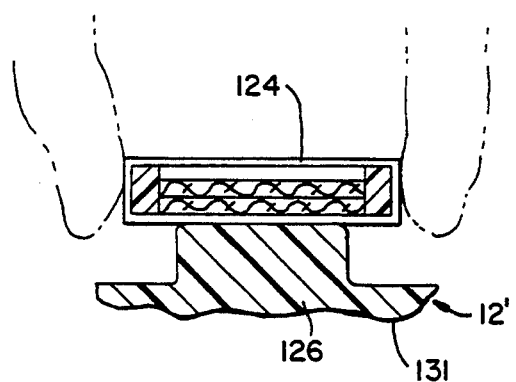
FIG. 6 is a cross sectional view of a retaining strap of FIG. 4, along lines 6—6 of FIG. 4, showing the plateau attached to the anterior coil form for raising the buckles.

Referring also now to FIG. 6, each of the buckles 124 rests on a plateau 126 extending outward from the top of the shell 131 of the anterior coil 12' generally along its circumference of curvature. The plateau 126 is of suitable height to support the buckle 124 above the surface of the shell 131 to permit the buckle 124 to be readily grasped for release.

Figure 9:
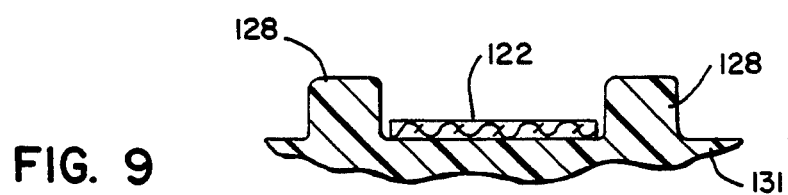
FIG. 9 is a cross sectional view of a retaining strap of FIG. 4, along lines 9—9 of FIG. 4, showing ridges attached to the anterior coil form for guiding the straps.

Referring also to FIG. 9, toward the lateral edges of the shell 131 the straps 122 are received within a pair of laterally extending rails 128 formed within the upper surface of the shell 131 of the anterior coil 12' so as to guide the straps 122 along lines of circumference of the cylinder of the hemicylindrical shape of the shells 131, during tightening of the buckle 124. The rails 128 promote even pressure by the straps 122 on the shells 131 improving the alignment of the shells 131 when supported on the bilaterally symmetric patient.

Referring now to FIGS. 5(a) through 5(d), the topologies of the anterior loop 44' and posterior loop 46' are electrically similar to the coils shown in FIGS. 3(a) through 3(d), however, following a more regular cylindrical shape. Conductors 38' and 37' are generally arcs of a circle conforming to the cylindrical shape of their shells 131 and connected by straight conductors 39' and 40' corresponding to conductors 39 and 40 as discussed before. Thus, the posterior loop 46' conforms substantially to the outer surface of a cylinder.

The conductors of anterior loop 44" corresponding to loops 64' and segment 66' are a mirror image of the loop 46' also conforming to a cylindrical surface with element 41' being a simple straight segment between segments 66' which are arcs of a circle.

The above description has been that of a preferred embodiment of the present invention. It will occur to those who practice the art that many modifications may be made without departing from the spirit and scope of the invention. For example, the two loops of the posterior coil 46 may be physically separate, provided they are substantially adjacent and have their signals combined as described. Clearly, the position of the anterior and posterior loops 44 and 46 may be reversed. Further, it will be apparent from this description that the present coil design may be used not only in receive only coils but in coils that also transmit the exciting RF MRI pulse. In order to apprise the public of the various embodiments that may fall within the scope of the invention, the following claims are made.

I claim:

1. An NMR probe for obtaining a signal from precessing nuclei within an imaging volume, the probe comprising:
    a first coil positioned adjacent to the imaging volume and having a first reception pattern which couples to a RF magnetic field of a first orientation within the imaging volume to produce a first signal;
    a second coil opposed substantially symmetrically to the first coil about the imaging volume, the second coil having at least one diametric conductor to divide the second coil into a pair of loops having a second reception pattern which couples to a RF magnetic field of a second orientation within the imaging volume to produce a second signal, the second orientation having an angular separation from the first orientation of substantially 90 degrees measured in the direction of the precession of the nuclei.

2. The NMR probe of claim 1 including additionally:
    a combiner means receiving the first and second signals for combining the first signal and the second signal wherein the second signal is shifted by 90° with respect to the first signal.

3. The NMR probe of claim 1 wherein the second coil lies within a curved surface substantially symmetric with respect to the diametric conductor.

4. The NMR probe of claim 3 wherein the first coil lies within a curved surface substantially symmetrically opposed to the diametric conductor.

5. A local coil for use in NMR imaging of a patient comprising:
    a first arched support having a first surface concave about a first arch axis and sized to fit against an anterior surface of the patient;
    a first coil having a first coil axis and being affixed to the first arched support to conform substantially to the first concave surface;
    a second arched support having a second surface concave about a second arch axis sized to fit against a posterior surface of the patient;
    a second coil having a second coil axis and being affixed to the second arched support to conform substantially to the second concave surface; and
    straps passing between the first and second arched support to draw the arched supports toward each other about the patient to one of a plurality of separation distances determined by a patient size supplying an even force to the patient wherein the first and second concave surfaces serve to support and align the first and second coils against the patient so that the first and second axes are substantially coaxial.

6. The local coil of claim 5 wherein the first arched support has a third surface positioned outward from the patient with respect to the first surface and wherein the third surface includes a plateau, and wherein the at least one flexible strap includes a buckle which may rest on top of the plateau to be spaced from the third surface when the strap is adjusted to draw the first and second arched supports together.

7. The local coil of claim 5 wherein the first and second coils have signal leads and including
    a combiner for receiving the first and second signal leads and combining signals on said leads; and
    a housing holding the combiner and attached by a hinge to the first arched support so that the housing may be hinged toward the patient about a hinge axis parallel to the patient's medial axis.

* * * * *